(12) United States Patent
Landschütze (10) Patent No.: US 6,940,001 B1
(45) Date of Patent: Sep. 6, 2005

(54) TRANSGENIC PLANT CELLS AND PLANTS HAVING MODIFIED ACTIVITY OF THE GBSSI AND OF THE BE PROTEIN

(75) Inventor: Volker Landschütze, Berlin (DE)

(73) Assignee: Bayer Cropscience GmbH, Frankfurt (DE)

( * ) Notice: Subject to any disclaimer, the term of this patent is extended or adjusted under 35 U.S.C. 154(b) by 0 days.

(21) Appl. No.: 09/636,289

(22) Filed: Aug. 10, 2000

(30) Foreign Application Priority Data

Aug. 12, 1999 (DE) .............................. 199 37 643

(51) Int. Cl.[7] ........................ C12N 15/82; C12N 15/29; C12N 5/10; A01H 5/00; C12P 19/04
(52) U.S. Cl. ...................... 800/284; 800/285; 800/286; 800/317.2; 435/101; 435/417; 435/419; 536/23.6; 536/24.5
(58) Field of Search ............................... 435/419, 417, 435/468, 320.1, 101; 536/23.6, 24.5; 800/284–286, 800/276, 287, 278, 317.2

(56) References Cited

U.S. PATENT DOCUMENTS

| | | | | |
|---|---|---|---|---|
| 5,856,467 A | | 1/1999 | Hofvander et al. ........... | 536/45 |
| 6,169,226 B1 | * | 1/2001 | Ek et al. ..................... | 800/284 |

FOREIGN PATENT DOCUMENTS

| | | |
|---|---|---|
| AU | 724164 | 11/1997 |
| CA | 2242398 | 7/1997 |
| DE | 196 18 125 | 11/1997 |
| DE | 196 53 176 | 8/1998 |
| DE | 198 36 098 | 2/2000 |
| WO | WO 97/26362 | 7/1997 |
| WO | WO 97/45545 | 12/1997 |
| WO | WO 98/27212 | 8/1998 |

OTHER PUBLICATIONS

Hohn et al. Proc. Natl. Acad. Sci. USA 96:8321-8323, Jul. 1999.*
Zhu et al. Proc. Natl. Acad. Sci. USA 96:8768-8773, Feb. 1999.*
Evans et al. Biochem. Soc. Trans. 20:3448, 1992.*
Mazzolini et al. Plant Mol. Biol. 20:715-731, 1992.*
Kull et al. J. Genet. + Breed. 49(1):65-76, Mar. 1995.*
Sattard et al. Carbohydrate Polymers 35(3/4) 155-168, 1998.*
Kuipers et al. Plant Cell 6(1):43-52, Jan. 1994.*
Flipse et al. Planta 198(3): 340-347, 1996.*
Macromol. Symp. 120, 1997, "Starch Biosynthesis and Modification of Starch Structure in Transgenic Plants", pp. 29-38, Kossmann et al.
Mol. Gen. Genet (1991) 225; pp. 289-296, Visser et al, "Inhibition of the Expression of the Gene for Granule-Bound Starch Synthase in Potato by Antisense Constructs".

* cited by examiner

Primary Examiner—David T. Fox
(74) Attorney, Agent, or Firm—Hunton & Williams LLP (57) ABSTRACT

Transgenic plant cells and plants are described which synthesize a starch which is modified in comparison to wild-type plant cells and plants and show a decrease in the activity of GBSSI and BE proteins. Furthermore, the modified starches obtainable from these plant cells and plants are described, and processes for their preparation.

20 Claims, 1 Drawing Sheet

FIG. 1

TRANSGENIC PLANT CELLS AND PLANTS HAVING MODIFIED ACTIVITY OF THE GBSSI AND OF THE BE PROTEIN

The present invention relates to transgenic plant cells and plants having a decreased activity of a GBSSI protein and a decreased activity of a BE protein, in particular of a BEI protein, and to means and processes for their production. Plant cells and plants of this type can synthesize a modified starch which has an amylopectin content of at least 90% and in comparison to starch from corresponding plants of the waxy phenotype an increased phosphate content and/or a decreased gelatinization temperature. The present invention therefore also relates to the starch synthesized from the plant cells and plants according to the invention and to processes for the production of this starch. The present invention further relates to the use of certain nucleic acid molecules for the production of plants which synthesize a starch having an amylopectin content of at least 90%, which in comparison to starch from corresponding plants of the waxy phenotype has an increased phosphate content and/or a decreased gelatinization temperature.

In view of the increasing importance which has recently been attributed to plant constituents as renewable raw material sources, it is one of the objects of biotechnological research to make an effort to adapt these plant raw materials to the requirements of the processing industry. In order to make possible application of renewable raw materials in as many areas of use as possible, it is moreover necessary to achieve a wide variety of substances.

In addition to oils, fats and proteins, polysaccharides are essential renewable raw materials from plants. In addition to cellulose, a central position in the case of the polysaccharides is occupied by starch, which is one of the most important storage substances in higher plants. Corn is one of the most interesting plants here, as it is the most important crop plant globally for starch production.

The polysaccharide starch is a polymer made from chemically uniform monomers, the glucose molecules. However, it is a very complex mixture of different forms of molecules which differ with respect to their degree of polymerization and the occurrence of branching of the glucose chains. Starch is therefore not a uniform raw material. A differentiation is made in particular between amylose starch, an essentially unbranched polymer of α-1,4-glycosidically linked glucose molecules, and amylopectin starch, which for its part is a complex mixture of differently branched glucose chains. The branchings come about owing to the occurrence of additional α-1,6-glycosidic links. In typical plants used for starch production, such as, for example, corn or potatoes, the synthesized starch consists to about 20%–30% of amylose starch and to about 70%–80% of amylopectin starch.

In order to make possible the widest possible use of starch, it appears desirable to make available plants which are able to synthesize modified starch which is particularly suitable for various intended uses. One possibility of making available plants of this type consists—in addition to breeding measures—in the controlled genetic modification of the starch metabolism of starch-producing plants by genetic engineering methods.

The ratio of amylopectin to amylose has a great influence on the physico-chemical properties of the starches and thus on the particular application possibilities of these starches. Since processes for the separation of these two components are very time-consuming and cost-intensive, processes of this type are no longer used on a large industrial scale (Young, A. H. in: Starch Chemistry and Technology. Eds. R. L. Whistler, J. N. BeMiller and E. F. Paschall. Academic Press, New York, 1984, 249–283). For a large number of applications, it would thus be desirable to have available starches which only contain one of the two polymers.

Hitherto, both mutants and plants produced by genetic engineering processes have been described which have a modified amylopectin/amylose ratio in comparison to corresponding wild-type plants. For example, a so-called "waxy" mutant from corn, which has a mutation in the gene coding for the granule-bound starch synthase 1, abbreviated: GBSSI (Akasuka and Nelson, J. Biol. Chem., 241, (1966), 2280–2285; Shure et al., Cell 35 (1983), 225–233), produces a starch which essentially consists of amylopectin. Below, a waxy starch is understood as meaning a starch having an amylopectin content of at least 90%.

For potatoes, genotypes were produced both by chemical mutagenesis of a haploid line (Hovenkamp-Hermelink et al., Theor. Appl. Genet., 225, (1987), 217–221) and by antisense inhibition of the gene for the GBSSI, whose starches essentially consist of amylopectin starch. In comparison to starches from corresponding wild-type plants, waxy potato starches of this type have no differences, with respect to the phosphate content, in the morphology of the starch granule or in the ion content (Visser et al., Starch/Stärke, 49, (1997), 438–443).

In addition to the amylose/amylopectin ratio, the functional properties of the starch are strongly influenced by the phosphate content, the molecular weight, the pattern of side chain distribution, the content of ions, the lipid and protein content etc. Examples of important functional properties which can be mentioned here are the solubility, the retrogradation behavior, the water-binding ability, the film-forming properties, the viscosity, the gelatinization properties, the stability etc. The size of the starch granule can also be of importance for various applications.

The phosphate content can basically be modified both by genetic engineering approaches (see, for example, WO 97/11188-A1; Safford et al., Carbohydrate Polymers 35, (1998), 155–168) and by subsequent chemical phosphorylation (see, for example, in: Starch Chemistry and Technology. Eds. R. L. Whistler, J. N. BeMiller and E. F. Paschall. Academic Press, New York, 1988, 349–364). However, as a rule chemical modifications are cost- and time-intensive.

Until now, it has not been possible to produce plant cells and plants which synthesize waxy starches having an increased phosphate content and/or decreased gelatinization temperature in comparison to starches from corresponding plant(s) (cells) of the waxy phenotype. Procedures for the production of plant cells and plants of this type and procedures for the production of starches of this type are as yet not described in the prior art.

Since the phosphate content of the starches influences their properties, it would be desirable to make available plant cells and plants which synthesize waxy starches having modified structural and/or functional properties in comparison to corresponding plant cells and plants of the waxy phenotype.

The present invention is thus based on the object of making available plant cells and plants which, in comparison to corresponding plant cells and plants of the waxy phenotype, synthesize starches having modified structural and/or functional properties, and waxy starch which differs in its structural and/or functional properties from other waxy starches and is thus better suited for general and/or specific intended uses.

This object is achieved by the provision of the embodiments described in the patent claims.

The present invention thus relates to transgenic plant cells which are genetically modified, the genetic modification leading to a decrease in the activity of one or more GBSSI proteins occurring endogenously in the plant cell and to a decrease in the activity of one or more BE proteins occurring endogenously in the plant cell, in comparison to corresponding non genetically modified plant cells of wild-type plants.

The genetic modification can be any genetic modification which leads to a decrease in the activity of an endogenous GBSSI protein and of a BE protein occurring in the plant cell in comparison to non genetically modified plant cells of corresponding wild-type plants.

The term "transgenic" in this connection means that the plant cells according to the invention differ in their genetic information from corresponding non genetically modified plant cells on account of a genetic modification, in particular the introduction of one or more foreign nucleic acid molecules.

The term "genetically modified" in this connection means that the genetic information of the plant cell is modified by introduction of one or more foreign nucleic acid molecules and that the presence or the expression of the foreign nucleic acid molecule leads to a phenotypic modification. "Phenotypic modification" preferably means a measurable modification in one or more functions of the cells; plant cells according to the invention in particular show a decrease in the expression of at least one endogenous GBSSI gene and at least one endogenous BE gene and/or a decrease in the activity of at least one GBSSI protein and at least one BE protein.

The term "GBSSI protein" is understood in the context of the present invention as meaning any protein which in contrast to the class of soluble starch synthases belongs to the class of granule-bound starch synthases isoform I (=GBSSI, EC 2.4.1.21). Plants in which the enzyme activity of this protein is greatly or completely reduced synthesize an essentially amylose-free, so-called waxy starch (Shure et al., (1983) supra; Hovenkamp-Hermelink et al., (1987), supra; Visser et al., Mol. Gen. Genet., 225, (1991), 289–296), so that this enzyme is ascribed a crucial role in the synthesis of amylose starch. Nucleic acid molecules which code for GBSSI proteins have been described for numerous plants, for example corn (Genbank Acc. No. AF079260, AF079261), wheat (Genbank Acc. No. AB019622, AB019623, AB019624), rice (Genbank Acc. No. AF092443, AF092444, AF031162), potatoes (Genbank Acc. No. X58453), barley (Genbank Acc. No. X07931, X07932). With the aid of these known nucleic acid molecules, it is possible for the person skilled in the art to isolate corresponding sequences from other organisms, in particular plant organisms, by standard processes, for example by heterologous screening.

In the context of the present invention, a branching enzyme or BE protein ($\alpha$-1,4-glucan: $\beta$-1,4-glucan 6-glycosyltransferase, E. C. 2.4.1.18) is understood as meaning a protein which catalyzes a transglycosylation reaction in which $\alpha$-1,4-linkages of an $\alpha$-1,4-glucan donor are hydrolyzed and the $\alpha$-1,4-glucan chains liberated are transferred to an $\alpha$-1,4-glucan acceptor chain and converted here into $\alpha$-1,6-linkages, preferably a BEI protein.

The term "BEI protein" designates a branching enzyme (BE) of isoform I. The designation of the isoforms follows the nomenclature proposed by Smith-White and Preiss, (Smith-White & Preiss, Plant Mol. Biol. Rep. 12, (1994), 67–71, Larsson et al., Plant Mol. Biol. 37, (1998), 505–511). In connection with the present invention, all enzymes which are structurally more similar to the BEI protein from corn (Baba et al., Biochem. Biophys. Res. Commun. 181 (1), (1991), 87–94; Kim et al. Gene 216, (1998), 233–243), i.e. at the level of the amino acid sequence, than the BEII isoform of the protein from corn (Genbank Acc. No AF072725, U65948) should be designated as isoform 1. In potato plants, the BEI gene is expressed mainly in the tubers and barely in the leaves (Larsson et al., Plant Mol. Biol. 37, (1998), 505–511).

Nucleic acid molecules which code for a BEI protein have been described for numerous plants, for example for corn (Genbank Acc. No. D 11081, AF 072724), rice (Genbank Acc. No. D11082), potatoes (various forms of the BEI gene (protein) from potato have been described, for example, in Khoshnoodi et al., Eur. J. Biochem. 242 (1), 148–155 (1996); Genbank Acc. No. Y 08786, Kossmann et al., Mol. Gen. Genet. 230, (1991), 39–44), peas (Genbank Acc. No. X80010). With the aid of these known nucleic acid molecules, it is possible for the person skilled in the art to isolate corresponding sequences from other organisms, in particular plant organisms, by standard processes, for example by heterologous screening.

The present invention further relates to transgenic plant cells which are genetically modified, the genetic modification consisting in the introduction of one or more foreign nucleic acid molecules, whose presence and/or expression leads to a decrease in the activity of GBSSI and BE proteins, in comparison to corresponding non genetically modified plant cells of wild-type plants.

The production of plant cells of this type according to the invention having a decreased activity of a GBSSI and of a BE protein can be acheived by means of various procedures known to the person skilled in the art, e.g. by means of those which lead to inhibition of the expression of endogenous genes which encode a GBSSI protein or a BE protein. These include, for example, the expression of a corresponding antisense RNA, the provision of molecules or vectors which mediate a cosuppression effect, the expression of a correspondingly constructed ribozyme which specifically cleaves transcripts which encode a GBSSI protein or a BE protein, or so-called "in-vivo mutagenesis". All these procedures are based on the introduction of one or more foreign nucleic acid molecules into the genome of plant cells.

The term "foreign nucleic acid molecule" is understood as meaning a nucleic acid molecule of the type which either does not occur naturally in corresponding plant cells, or which, in the actual spatial arrangement, does not occur naturally in the plant cells or which is located at a site in the genome of the plant cell in which it does not occur naturally. The foreign nucleic acid molecule is preferably a recombinant nucleic acid molecule which consists of various elements whose combination or specific spatial arrangement does not occur naturally in plant cells.

The "foreign nucleic acid molecule" can be, for example, a so-called "double construct", by which is understood a single vector for plant transformation which contains both the genetic information for the inhibition of the expression of one or more endogenous GBSSI genes and for the inhibition of the expression of one or more BE genes or whose presence and/or expression leads to a decrease in the activity of one or more GBSSI proteins and one or more BE proteins.

In a further embodiment of the invention, not only a single specific vector, but a number of different foreign nucleic acid molecules, is introduced into the genome of the plant cell, one of these foreign nucleic acid molecules being a DNA molecule which, for example, is a cosuppression construct which brings about a decrease in the expression of endogenous GBSSI genes, and a further foreign nucleic acid molecule being a DNA molecule which, for example, encodes an antisense RNA which brings about a decrease in the expression of endogenous BE genes. In principle, in the construction of the foreign nucleic acid molecules, however, the use of any combination of antisense, cosuppression and ribozyme constructs or in-vivo mutagenesis which leads, in the genetically modified plant cell, to a simultaneous decrease in the gene expression of endogenous GBSSI and BE genes or which leads to a simultaneous decrease in the activity of GBSSI and BE proteins is suitable.

The foreign nucleic acid molecules can here be introduced into the genome of the plant cell simultaneously ("cotransformation") or successively, i.e. chronologically one after the other ("supertransformation"). A number of foreign nucleic acid molecules can be present in combined form, for example, in a "double construct".

In one embodiment of the invention, at least one antisense RNA is expressed in plant cells for the reduction of the activity of one or more GBSSI proteins and/or one or more BE proteins.

For this, for example, a DNA molecule can be used which comprises the entire sequence coding for a GBSSI protein and/or a BE protein including flanking sequences, if present, and DNA molecules which only comprise parts of the coding sequence, these parts being long enough to bring about an antisense effect in the cells. In general, suitable sequences are those up to a minimum length of 15 bp, preferably of a length of 100–500 bp, for an efficient antisense-inhibition, in particular sequences having a length of over 500 bp. As a rule, DNA molecules are used for this which are shorter than 5000 bp, preferably sequences which are shorter than 2500 bp.

Also possible is the use of DNA sequences which have a high degree of homology to the sequences occurring endogenously in the plant cell, which encode a GBSSI protein or a BE protein. The minimal homology should be greater than about 65%. The use of sequences having homologies between 95 and 100% is preferred.

In a further embodiment, the decrease in the GBSSI and/or the BE activity in the plant cells is achieved by a cosuppression effect. The procedure is known to the person skilled in the art and is described, for example, in Jorgensen (Trends Biotechnol. 8 (1990), 340–344), Niebel et al., (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al., (Mol. Gen. Genet. 248 (1995), 311–317), de Borne et al. (Mol. Gen. Genet. 243 (1994), 613–621). As in the case of the antisense technology, both DNA molecules which code for the entire coding region of the GBSSI and/or of the BE protein, and DNA molecules which comprise only parts of the coding sequence, can be used.

Also suitable is the use of DNA sequences which have a high degree of homology to the sequences occurring endogenously in the plant cell, which encode GBSSI and/or BE proteins. The minimal homology should be greater than about 65%. The use of sequences with homologies between 95 and 100% is preferred. For example, for the inhibition of the BEI gene from potatoes, a DNA sequence coding for a BEI protein is preferably used, in particular from potatoes, Kossmann et al. (Mol. Gen. Genet. 230, (1991), 39–44).

The expression of ribozymes for decreasing the activity of certain enzymes in cells is known to the person skilled in the art and is described, for example, in EP-B1 0321201. The expression of ribozymes in plant cells has been described, for example, in Feyter et al. (Mol. Gen. Genet. 250, (1996), 329–338).

The decrease in the GBSSI and/or the BE activity in the plant cells according to the invention can furthermore also be achieved by so-called "in vivo mutagenesis", in which a hybrid RNA/DNA oligonucleotide ("chimeroplast") is inserted into cells by means of cell transformation (Kipp, P. B. et al., Poster Session at the 5$^{th}$ International Congress of Plant Molecular Biology, Sep. 21st–27th, 1997, Singapore; R. A. Dixon and C. J. Arntzen, Meeting report in "Metabolic Engineering in Transgenic Plants", Keystone Symposia, Copper Mountain, Colo., USA, TIBTECH 15, (1997), 441–447; International Patent Application WO 9515972-A1; Kren et al., Hepatology 25, (1997), 1462–1468; Cole-Strauss et al., Science 273, (1996), 1386–1389).

A part of the DNA component of the RNA/DNA oligonucleotide is homologous to a nucleic acid sequence of an endogenous GBSSI gene and/or BE gene, but in comparison to the nucleic acid sequence of the endogenous GBSSI gene and/or BE gene has a mutation or contains a heterologous region which is enclosed by the homologous regions.

By means of base pairing of the homologous regions of the RNA/DNA oligonucleotide and of the endogenous nucleic acid molecule, followed by homologous recombination, the mutation or heterologous region contained in the DNA component of the RNA/DNA oligonucleotide can be transferred to the genome of a plant cell. This leads to a decrease in the activity of a GBSSI protein and/or of a BE protein. It is further known to the person skilled in the art that it can achieve the activity of a GBSSI protein and/or of a BE protein by the expression of nonfunctional derivatives, in particular trans-dominant mutants of such proteins and/or by the expression of antagonists/inhibitors of such proteins. Antagonists/inhibitors of such proteins include, for example, antibodies, antibody fragments or molecules having similar binding properties. For example, a cytoplasmic scFv antibody was employed in order to modulate the activity of the phytochrome A protein in genetically modified tobacco plants (Owen, Bio/Technology 10 (1992), 7904; Review: Franken, E, Teuschel, U. and Hain, R., Current Opinion in Biotechnology 8, (1997), 411–416; Whitelam, Trends Plant Sci. 1 (1996), 268–272).

The present invention therefore relates to transgenic plant cells having an activity of endogenous GBSSI and BE proteins which is decreased in comparison to unmodified plant cells and which contain one or more foreign nucleic acid molecules, selected from the group consisting of a) a DNA molecule which leads to the synthesis of at least one antisense RNA which brings about a decrease in the expression of endogenous genes which encode a GBSSI and/or a BE protein;

b) a DNA molecule which leads, via a cosuppression effect, to a decrease in the expression of endogenous genes which encode a GBSSI and/or a BE protein;

c) a DNA molecule which leads to the synthesis of at least one ribozyme which specifically cleaves transcripts of genes which encode a GBSSI and/or a BE protein; and d) a nucleic acid molecule which, on account of in-vivo mutagenesis, leads to a mutation or insertion of a heterologous nucleic acid sequence into at least one gene encoding endogenous GBSSI and/or BE protein, the mutation or insertion bringing about a decrease in the expression of the GBSSI gene and/or of the BE gene, or the synthesis of an inactive GBSSI and/or inactive BE protein.

The expression "decrease in the activity" in the context of the present invention means a decrease in the expression of endogenous genes which encode a GBSSI and a BE protein, a decrease in the amount of GBSSI and BE protein in the cells and/or a decrease in the enzymatic activity of the GBSSI and of the BE protein in the cells.

The decrease in the expression can be determined, for example, by measurement of the amount of transcripts encoding GBSSI and BE protein, e.g. by Northern blot analysis. A decrease in this case preferably means a decrease in the amount of transcripts in comparison to corresponding non genetically modified cells by at least 50%, preferably by at least 70%, particularly preferably by at least 85% and very particularly preferably by at least 95%.

The decrease in the amount of GBSSI and BE protein can be determined, for example, by Western blot analysis. A decrease in this case preferably means a decrease in the amount of GBSSI and BE protein in comparison to corresponding non genetically modified cells by at least 50%, preferably by at least 70%, particularly preferably by at least 85% and very particularly preferably by at least 95%.

The decrease in the enzymatic activity of the GBSSI protein can be determined, for example, by the method described by Kuipers et al., Plant Mol. Biol., 26 (1994), 1759–1773. The decrease in the enzymatic activity of the BE protein can be determined by the method described by Safford et al., Carbohydrate Polymers 35, (1998), 155–168. A decrease in the enzymatic activity in comparison to corresponding non genetically modified cells in this case preferably means a decrease by at least 50%, preferably by at least 70%, particularly preferably by at least 85% and very particularly preferably by at least 95%.

The transgenic plant cells according to the invention synthesize a modified starch whose physicochemical properties, for example, in particular the amylose/amylopectin ratio, the degree of branching, the average chain length, the phosphate content, the viscosity behavior, the starch granule size and/or the starch granule form can be modified in comparison to starch synthesized in wild-type plants such that this is better suited to specific intended uses.

It has surprisingly been found that in the case of plant cells in which the activity of the GBSSI and of the BEI protein is decreased, the composition of the starch is modified in such a manner that it comprises not only an amylopectin content of at least 90%, but additionally also an increased phosphate content in comparison to plant cells of corresponding plants of the waxy phenotype. This increased phosphate content acts on the functional properties of the starch such that this is better suited to specific intended uses.

The present invention also relates to transgenic plant cells which contain a modified starch having an amylopectin content of at least 90%, preferably of at least 93%, particularly preferably of at least 95% and especially preferably of at least 97% and, in comparison to starch from plant cells of corresponding plants of the waxy phenotype, have an increased phosphate content.

The amylopectin content can in this case be determined by the method of Hovenkamp-Hermelink et al. (Potato Research 31, (1988), 241–246) described in the examples for potato starch. This method is also applicable to isolated starches of other plant species. Procedures for the isolation of starches are known to the person skilled in the art.

The expression "increased phosphate content" in connection with the present invention means that the total content of covalently bonded phosphate and/or the content of phosphate in the C-6 position of the starch synthesized in the plant cells according to the invention is increased by at least 30%, preferably by at least 50%, particularly preferably by at least 75%, in particular by at least 100% in comparison to plant cells of corresponding plants of the waxy phenotype.

The total phosphate content or the content of phosphate in the C-6 position can be determined by the method described below.

The expression "corresponding plants of the waxy phenotype" is intended in connection with the present invention to mean comparable plants, preferably plants of the same original variety, i.e. the variety from which the transgenic plants according to the invention have been produced by introduction of the genetic modification described above. Plants of the waxy phenotype furthermore contain plant cells which synthesize a starch having an amylopectin content of at least 90%, preferably of at least 93%, particularly preferably of at least 95% and especially preferably of at least 97%. In addition, plants of the waxy phenotype have a decreased enzymatic activity of the GBSSI protein in comparison to plant cells of wild-type plants.

In a further embodiment, the present invention also relates to transgenic plant cells which contain a modified starch having an amylopectin content of at least 90%, preferably of at least 93%, particularly preferably of at least 95% and especially preferably of at least 97%, have an increased phosphate content in comparison to starch from plant cells of corresponding plants of the waxy phenotype and/or have a decreased gelatinization temperature in comparison to starches from plant cells or corresponding plants of the waxy phenotype.

Figure 1:
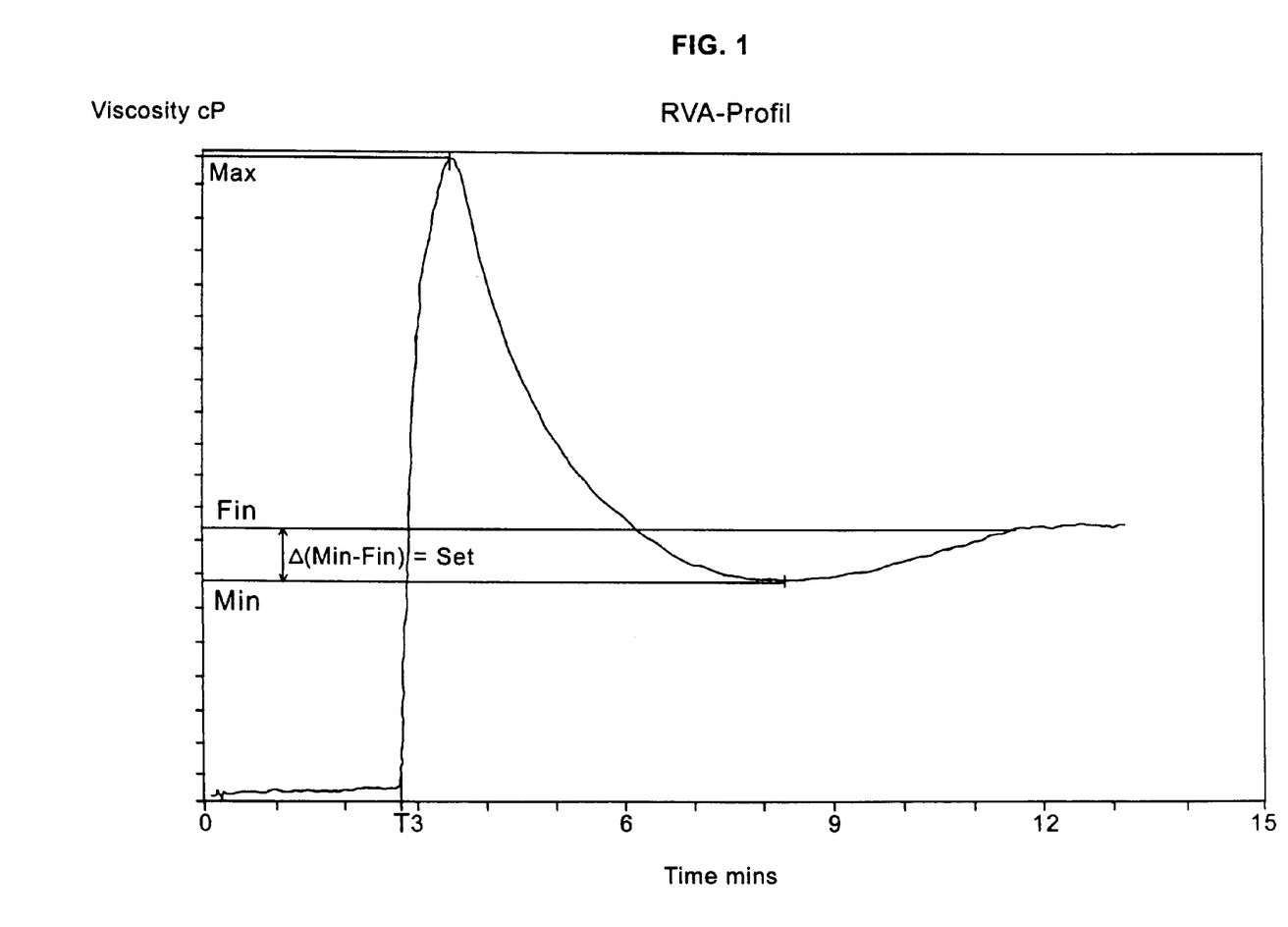
FIG. 1: Schematic representation of an RVA profile
  The following methods were used in the examples.

The gelatinization temperature is intended in the context of the present invention to mean the temperature T which can be determined from a viscosity profile (see FIG. 1) which can be obtained by means of a Rapid Visco Analyzer (RVA) (Newport Scientific Pty Ltd, Investment Support Group, Warriewood, NSW 2102, Australia). The viscosity profile is in this case plotted according to the protocol described below. The gelatinization temperature designates that temperature at which the viscosity begins to increase significantly on account of the swelling of the starch granules. The gelatinization temperature is determined by means of the gradient of the viscosity curve as a function of time. If the gradient of the curve is greater than 1.2 (hits value is specified by the user on the RVA apparatus), the computer program identifies the temperature measured at this time as the gelatinization temperature.

The term "decreased gelatinization temperature" in this case means that the gelatinization temperature is decreased by at least 0.5° C., preferably by at least 1.5° C., particularly preferably by at least 3° C. and especially preferably by at least 5° C. in comparison to starches from plant cells of corresponding plants of the waxy phenotype.

The observation that the starches of the plant cells according to the invention have a decreased gelatinization temperature in comparison to starches from plant cells of corresponding plants of the waxy phenotype is therefore particularly surprising, because Safford et al. (Carbohydrate Polymers 35, (1998), 155–168) were able to show that a phosphate content which was increased in comparison to starches from wild-type plants, which can be produced by an antisense inhibition of a BEI protein in potato plants, leads to starches having an increased viscosity onset temperature.

The viscosity onset temperature is a variable related to the gelatinization temperature, which in contrast to the gelatinization temperature is based on the method of differential scanning calorimetry (=DSC).

A large number of techniques are available for the introduction of DNA into a plant host cell. These techniques include the transformation of plant cells with T DNA using *Agrobacterium tumefaciens* or *Agrobacterium rhizogenes* as transforming agents, the fusion of protoplasts, injection, the electroporation of DNA, the incorporation of the DNA by means of the biolistic approach and other possibilities.

The use of the agrobacteria-mediated transformation of plant cells has been intensively investigated and adequately described in EP-A-120516; Hoekema, in: The Binary Plant Vector System Offsetdrukkerij Kanters B. V., Alblasserdam (1985), Chapter V; Fraley et al., Crit. Rev. Plant Sci. 4, 146 and An et al. EMBO J. 4, (1985), 277–287. For the transformation of potatoes, see, for example, Rocha-Sosa et al., EMBO J. 8, (1989), 29–33).

The transformation of monocotyledonous plants by means of vectors based on *Agrobacterium* has also been described (Chan et al., Plant Mol. Biol. 22, (1993), 491–506; Hiei et al., Plant J. 6, (1994) 271–282; Deng et al., Science in China 33, (1990), 28–34; Wilmink et al., Plant Cell Reports 11, (1992), 76–80; May et al., Bio/Technology 13, (1995), 486492; Conner and Domisse, Int. J. Plant Sci. 153 (1992), 550–555; Ritchie et al., Transgenic Res. 2, (1993), 252–265). An alternative system for the transformation of monocotyledonous plants is transformation by means of the biolistic approach (Wan and Lemaux, Plant Physiol. 104, (1994), 37–48; Vasil et al., Bio/Technology 11 (1993), 1553–1558; Ritala et al., Plant Mol. Biol. 24, (1994), 317–325; Spencer et al., Theor. Appl. Genet. 79, (1990), 625–631), protoplast transformation, the electroporation of partially permeabilized cells, and the incorporation of DNA by means of glass fibers. In particular, the transformation of corn is repeatedly described in the literature (cf., for example, WO 95/06128, EP 0513849, EP 0465875, EP 292435; Fromm et al., Biotechnology 8, (1990), 833–844; Gordon-Kamm et al., Plant Cell 2, (1990), 603–618; Koziel et al., Biotechnology 11 (1993), 194–200; Moroc et al., Theor. Appl. Genet. 80, (1990), 721–726).

The successful transformation of other types of cereal has also already been described, e.g. for barley (Wan and Lemaux, supra; Ritala et al., supra.; Krens et al., Nature 296, (1982), 72–74) and for wheat (Nehra et al., Plant J. 5, (1994), 285–297).

Generally, any promoter which is active in plant cells is suitable for the expression of the foreign nucleic acid molecule(s). In this case, the promoter can be chosen such that expression takes place constitutively in the plants according to the invention or only in a certain tissue, at a certain point in time of plant development or at a point in time determined by external influences. With respect to the plant, the promoter can be homologous or heterologous.

Useful promoters are, for example, the promoter of the 35S RNA of cauliflower mosaic virus and the ubiquitin promoter from corn for constitutive expression, the patatin gene promoter B33 (Rocha-Sosa et al., EMBO J. 8 (1989), 23–29) for tuber-specific expression in potatoes or a promoter which ensures expression only in photosynthetically active tissues, e.g. the ST-LS1 promoter (Stockhaus et al., Proc. Natl. Acad. Sci. USA 84 (1987), 7943–7947; Stockhaus et al., EMBO J. 8 (1989), 2445–2451), the Ca/b promoter (see, for example, U.S. Pat. No. 5,656,496, U.S. Pat. No. 5,639,952, Bansal et al., Proc. Natl. Acad. Sci. USA 89, (1992), 3654–3658) and the Rubisco SSU promoter (see, for example, U.S. Pat. No. 5,034,322, U.S. Pat. No. 4,962, 028) or for endosperm-specific expression of the glutelin promoter (Leisy et al., Plant Mol. Biol. 14, (1990), 41–50; Zheng et al., Plant J. 4, (1993), 357–366; Yoshihara et al., FEBS Left. 383, (1996), 213–218), the Shrunken-1 promoter (Werr et al., EMBO J. 4, (1985), 1373–1380), the HMG promoter from wheat, the USP promoter, the phaseolin promoter or promoters of zein genes from corn (Pedersen et al., Cell 29, (1982), 1015–1026; Quatroccio et al., Plant Mol. Biol. 15 (1990), 81–93).

The expression of the foreign nucleic acid molecule(s) is particularly of advantage in those organs of the plant which store starch. Such organs are, for example, the tuber of the potato plant or the granules or the endosperm of corn, wheat or rice plants. Promoters are therefore preferably used which mediate the expression in these organs.

However, promoters can also be used which are only activated at a point in time determined by external influences (see, for example, WO 93/07279-A1). Of particular interest in this case can be promoters of heat-shock proteins which allow simple induction. Seed-specific promoters, such as, for example, the USP promoter from *Vicia faba*, which guarantees seed-specific expression in *Vicia faba* and other plants (Fiedler et al., Plant Mol. Biol. 22, (1993), 669–679; Bäumlein et al., Mol. Gen. Genet. 225, (1991), 459–467), can furthermore [lacuna]. Fruit-specific promoters can also be employed, such as described, for example, in WO 91/01373-A1.

A termination sequence can furthermore be present which serves for the correct ending of transcription and the addition of a poly-A tail to the transcript, which is attributed a function in the stabilization of the transcripts. Elements of this type are described in the literature (cf., for example, Gielen et al., EMBO J. 8 (1989), 23–29) and are arbitrarily exchangeable.

The plant cells according to the invention can belong to any desired plant species, i.e. both to monocotyledonous and to dicotyledonous plants. Preferably, they are plant cells from useful agricultural plants, i.e. from plants which are cultured by man for food purposes or for technical, in particular industrial, purposes. The invention preferably relates to fiber-forming (e.g. flax, hemp, cotton), oil-storing (e.g. oilseed rape, sunflower, soybeans), sugar-storing (e.g. sugar beet, sugar cane, sorghum) and protein-storing plants (e.g. leguminous plants).

In a further preferred embodiment, the invention relates to feed plants (e.g. feed and pasture grasses (alfalfa, clover etc.)), and vegetable plants (e.g. tomato, lettuce, chicory).

In a particularly preferred embodiment, the invention relates to plant cells from starch-storing plants (e.g. wheat, barley, oats, rye, potatoes, corm, rice, peas, cassava); plant cells from potato are particularly preferred.

The plant cells according to the invention can be used for the regeneration of whole plants.

The plants obtainable by regeneration of the transgenic plant cells according to the invention are likewise the subject of the present invention. The present invention further relates to plants which contain the transgenic plant cells described above. The transgenic plants can in principle be plants of any desired plant species, i.e. both monocotyledonous and dicotyledonous plants. They are preferably useful plants, i.e. plants which are cultivated by man for food purposes or for technical, in particular industrial, purposes. The invention preferably relates to plant cells from fiber-forming (e.g. flax, hemp, cotton), oil-storing (e.g. oilseed rape, sunflower, soybeans)), sugar-storing (e.g. sugar beet, sugar cane, sorghum) and protein-storing plants (e.g. leguminous plants).

In a further preferred embodiment, the invention relates to feed plants (e.g. feed and pasture grasses (alfalfa, clover etc.) and vegetable plants (e.g. tomato, lettuce, chicory).

In a particularly preferred embodiment the invention relates to starch-storing plants (e.g. wheat, barley, oats, rye, potatoes, corn, rice, peas, cassava); potato plants are particularly preferred.

The present invention also relates to a process for the production of a transgenic plant cell or plant which synthesizes a modified starch, where (a) a plant cell is genetically modified by the introduction of one or more foreign nucleic acid molecules, whose presence and/or expression lead/leads to a decrease in the activity of a protein having the activity of a GBSSI protein and to a decrease in the activity of a protein having the activity of a BE protein;

and in the case of the production of a plant (b) a plant is regenerated from the cell produced according to step a); and, if appropriate, further plants are produced from the plants produced according to step b).

The present invention also relates to a process for the production of a transgenic plant cell or plant whose starch has an amylopectin content of at least 90% and an increased phosphate content in comparison to starch from corresponding plants of the waxy phenotype, where (a) a plant cell is genetically modified by the introduction of one or more foreign nucleic acid molecules, whose presence or whose expression leads to a decrease in the activity of a protein having the activity of a GBSSI protein and to a decrease in the activity of a protein having the activity of a BEI protein;

and in the case of the production of a plant (b) a plant is regenerated from the cell produced according to step a); and, if appropriate, further plants are produced from the plants produced according to step b).

The present invention furthermore relates to a process for the production of a transgenic plant cell or plant whose starch has an amylopectin content of at least 90% and which has an increased phosphate content and/or a decreased gelatinization temperature T in comparison to starch from corresponding plants of the waxy phenotype, where (a) a plant cell is genetically modified by the introduction of one or more foreign nucleic acid molecules whose presence or whose expression leads to a decrease in the activity of a protein having the activity of a GBSSI protein and to a decrease in the activity of a protein having the activity of a BEI protein;

and in the case of the production of a plant (b) a plant is regenerated from the cell produced according to a); and, if appropriate, further plants are produced from the plant produced according to step b).

The expressions "increased phosphate content" and "decreased gelatinization temperature" are as already defined above in this connection.

For the genetic modification introduced according to step a), the same applies as has already been explained above in a different connection with the plants according to the invention.

The regeneration of plants according to step b) can be carried out by methods known to the person skilled in the art.

The production of further plants according to step b) of the process according to the invention can be carried out, for example, by vegetative reproduction (for example by means of cuttings, tubers or by means of callus culture and regeneration of whole plants) or by sexual reproduction. Sexual reproduction in this case preferably takes place in a controlled manner, i.e. selected plants having certain properties are crossed with one another and reproduced. Of course, it is known to the person skilled in the art that, for the production of the plant cells and plants according to the invention, he/she can also use transgenic plants in which the activity of one of the abovementioned proteins has already been decreased and which, in accordance with the process according to the invention, only have to be genetically modified inasmuch as the activity of the second protein is also decreased.

It is furthermore known to the person skilled in the art that the super-transformation described above is not necessarily carried out in primary transformants, but preferably in previously selected stable transgenic plants which advantageously have already been tested by means of appropriate experiments for, for example, fertility, stable expression of the foreign gene, hemi- and homozygotism etc.

The present invention also relates to the plants obtainable by the process according to the invention.

The present invention also relates to reproductive material of plants according to the invention and to the transgenic plants produced in accordance with the process according to the invention. The term reproductive material in this case includes those constituents of the plants which are suitable for the production of descendants by a vegetative or generative route. For vegetative reproduction, those suitable are, for example, cuttings, callus cultures, rhizomes or tubers. Other reproductive material includes, for example, fruits, seeds, seedlings, protoplasts, cell cultures, etc.

Preferably, the reproductive material comprises tubers and seeds. The present invention furthermore relates to the use of one or more foreign nucleic acid molecules which encode a protein having the enzymatic activity of a GBSSI protein and a protein having the enzymatic activity of a BE protein or the use of fragments of said nucleic acid molecules for the production of plant cells or plants which synthesize a modified starch.

In a further preferred embodiment, the present invention relates to the use of one or more foreign nucleic acid molecules which encode(s) a protein having the enzymatic activity of a GBSSI protein and a protein having the enzymatic activity of a BEI protein or the use of fragments of said nucleic acid molecule(s) for the production of plants which synthesize a modified starch which, in comparison to starch from corresponding plants of the waxy-phenotype, has an increased phosphate content and/or a decreased gelatinization temperature.

The term "fragment(s)" in this connection is intended to mean a part of the foreign nucleic acid molecule(s) which can code, for example, for a functionally active part of the proteins described. The fragment can furthermore also code for an antisense or a cosuppression mRNA or for a ribozyme. When using the fragments, care must be taken that only those fragments are used which lead to a decrease in the enzymatic activity of a GBSSI and/or of a BE or of a BEI protein.

In a further embodiment, the present invention relates to the use of one or more foreign nucleic acid molecules for the production of plants which synthesize a starch having an amylopectin content of at least 90%, which, in comparison to starch from corresponding plants of the waxy phenotype, has an increased phosphate content and/or a decreased gelatinization temperature, the foreign nucleic acid molecule being a molecule or the foreign nucleic acid molecules being a number of molecules selected from the group consisting of:

a) DNA molecules which encode at least one antisense RNA which brings about a decrease in the expression of endogenous genes encoding GBSSI and/or BEI proteins;

b) DNA molecules which via a cosuppression effect lead to a decrease in the expression of endogenous genes encoding GBSSI and/or BEI proteins;

c) DNA molecules which encode at least one ribozyme which specifically cleaves transcripts of endogenous genes encoding GBSSI and/or BEI proteins; and d) nucleic acid molecules introduced by means of in-vivo mutagenesis, which lead to a mutation or an insertion of a heterologous sequence in one or more endogenous GBSSI and/or BEI proteins, the mutation or insertion bringing about a decrease in the expression of the GBSSI gene and/or the BEI gene or the synthesis of an inactive GBSSI protein and/or an inactive BEI protein.

As already explained above, the foreign nucleic acid molecules can be introduced into the genome of the plant cell simultaneously or else successively. In this case, the simultaneous introduction of the foreign nucleic acid molecules is time- and cost-saving, i.e. cotransformation in which, in a transformation experiment in accordance with the process according to the invention described above, (a) nucleic acid molecule(s) is/are preferably introduced into the plant cell, whose presence and, if appropriate, expression leads/lead to a decrease in the activity of a protein having the activity of a GBSSI protein and to a decrease in the activity of a protein having the activity of a BE protein, preferably of a BEI protein. The present invention therefore also relates to compositions which contain at least one of the nucleic acid molecules described above. Preferably, their introduction into plant cells leads to a decrease in the activity of a GBSSI protein and to a decrease in the activity of a protein having the activity of a BE protein, preferably of a BEI protein. In this case, in the composition according to the invention the nucleic acid molecules whose respective presence in the plant cell leads to a decrease in the activities of GBSSI and of BE proteins, preferably of a BEI protein, can be included either separately or together in a recombinant nucleic acid molecule. In the first case, the composition according to the invention can contain, for example, two or more recombinant vectors whose joint presence in the plant cell leads to said phenotype. In the second case, which is preferred according to the invention, a recombinant nucleic acid molecule contains the genetic information which leads to a decrease in the activity of a GBSSI and of a BE protein, preferably of a BEI protein. For example, in such a recombinant nucleic acid molecule the nucleic acid molecules described above, whose presence in a plant cell leads to a decrease in the activity of a GBSSI or of a BE or BEI protein, can be present as a chimeric gene or as separate genes. Numerous examples of such double or multiple constructs are described in the technical literature. The aforementioned recombinant nucleic acid molecules can be present in any desired host cell which thereby is likewise a subject of the present invention. A further advantage in the use of such double or multiple constructs is that plant cells and plants according to the invention can be identified more easily, for example by means of an appropriate choice of PCR primers or Southern blots. The plant cells and plants according to the invention are therefore preferably characterized by the presence of such double or multiple constructs.

On account of the expression of a foreign nucleic acid molecule or of a number of foreign nucleic acid molecules whose presence or whose expression leads to a decrease in the activity of a GBSSI protein and to a decrease in the activity of a BE protein, preferably of the BEI protein, in comparison to corresponding non genetically modified plant cells of wild-type plants, the transgenic plant cells and plants according to the invention synthesize a starch whose physicochemical properties, in particular the amylose/amylopectin ratio and/or the phosphate content and/or the gelatinization behavior, are modified in comparison to starch synthesized in wild-type plants.

The present invention therefore relates to starch which is obtainable from the transgenic plant cells, plants and reproductive material according to the invention.

Furthermore, the present invention also relates to starches which have an amylopectin content of at least 90% and a phosphate content which is increased in comparison to starch from corresponding plants of the waxy phenotype by at least 30%, preferably by at least 50%, particularly preferably by at least 75%, in particular by at least 100%, in comparison to plant cells of corresponding plants of the waxy phenotype.

On account of the increased phosphate content, the starches according to the invention have the advantage over conventional waxy starches that they are better suited to certain intended uses on account of their modified physicochemical properties. On account of the increased phosphate content, for this the starches according to the invention subsequently do not have to be or have to be less strongly chemically phosphorylated in comparison to conventional waxy starches.

The starches according to the invention preferably differ from chemically phosphorylated monophosphate waxy starches in their structural/functional properties.

Phosphorylated waxy starches are particularly suitable for use for all thickenings without a skin or gel formation in the desserts, delicacies and ready-to-serve meals area, especially also for deep-freeze products. In technical areas, monostarch phosphates are in some cases used for paper manufacture, additionally as sizing, flocculating and flotation agents and as a detergent additive.

In a further embodiment, the present invention also relates to starches which have an amylopectin content of at least 90%, a phosphate content which is increased in comparison to starch from corresponding plants of the waxy phenotype by at least 30% and/or a decreased gelatinization temperature T.

The term "decreased gelatinization temperature" in this connection is intended as having the meaning already defined above.

In connection with certain applications and technical processes, a decreased gelatinization temperature allows the saving of heat energy and/or simplified process implementation.

In a particularly preferred embodiment, the present invention relates to starches from potato plants which have an amylopectin content of at least 90%, a phosphate content which is increased in comparison to starch from corresponding plants of the waxy phenotype by at least 30% and/or a decreased gelatinization temperature T.

In comparison to native starch from corn, rice or wheat plants, native potato starches have an increased phosphate content, which predestines them for certain applications. Surprisingly, it is possible with the aid of the approach according to the invention to increase the phosphate content of waxy potato starches further so that the potato starches according to the invention, in comparison to potato starches from corresponding wild-type plants and/or in comparison to corresponding potato plants of the waxy phenotype, have a phosphate content which is increased by at least 30%, preferably by at least 50%, particularly preferably by at least 75% and in particular by at least 100%. Potato starches furthermore have the advantage over cereal starches (e.g. wheat, oats, corn, rice) that they have a low content of lipids and proteins.

In a further preferred embodiment of the invention, the potato starches are characterized by an amylopectin content of at least 93%, particularly preferably of at least 95% and especially preferably of at least 97% and/or by a phosphate content which is increased in comparison to starch from plant cells of corresponding plants of the waxy phenotype by at least 30%, preferably by at least 50%, particularly preferably by at least 75%, in particular by at least 100%, in comparison to plant cells of corresponding plants of the waxy phenotype and/or by a gelatinization temperature which is decreased in comparison to starch from plant cells of corresponding plants of the waxy phenotype by at least 0.5° C., preferably by at least 1.5° C., particularly preferably by at least 3° C. and especially preferably by at least 5° C.

In this connection, the terms "phosphate content" and "gelatinization temperature" are defined in the same manner as already described above.

The present invention furthermore relates to a process for the production of a modified starch comprising the step of extraction of the starch from a plant (cell) according to the invention described above and/or from starch-storing parts of such a plant. Preferably, such a process also includes the step of the harvesting of the cultivated plants and/or starch-storing parts of these plants before the extraction of the starch and particularly preferably furthermore the step of the cultivation of plants according to the invention before harvesting. Processes for the extraction of the starch from plants or from starch-storing parts of plants are known to the person skilled in the art. Processes for the extraction of the starch from various other starch-storing plants are furthermore described, e.g. in "Starch: Chemistry and Technology (ed.: Whistler, BeMiller and Paschall (1994), 2nd edition, Academic Press Inc. London Ltd; ISBN 0-12-746270-8; see, for example, chapter XII, pages 412–468: corn and sorghum starches: production; by Watson; chapter XIII, pages 469–479: tapioca, arrowroot and sago starches: production; by Corbishley and Miller; chapter XIV, pages 479–490: potato starch: production and uses; by Mitch; chapter XV, pages 491 to 506: wheat starch: production, modification and uses; by Knight and Oson; and chapter XVI, pages 507 to 528: rice starch: production and uses; by Rohmer and Klem; corn starch: Eckhoff et al., Cereal Chem. 73 (1996) 54–57, as a rule the extraction of corn starch on an industrial scale is achieved by so-called wet-milling). Appliances which are usually used in processes for the extraction of starch from plant material are separators, decanters, hydrocyclones, spray dryers and fluidized bed dryers.

The present invention furthermore relates to starch which is obtainable by the process according to the invention described above.

The starches according to invention can be subsequently modified by the processes known to the person skilled in the art and are suitable in unmodified or modified form for various uses in the foodstuffs or non foodstuffs area.

Basically, the possibilities of application of the starch can be subdivided into two large areas. One area includes the hydrolysis products of the starch, mainly glucose and glucan units, which are obtained by enzymatic or chemical processes. They serve as starting substances for further chemical modifications and processes, such as fermentation. For reduction of the costs, the simplicity and inexpensive carrying-out of a hydrolysis process can be of importance here. At present, it proceeds essentially enzymatically using amyloglucosidase. A saving of costs by lower use of enzymes would be conceivable. A structural modification of the starch, e.g. surface enlargement of the granule, or easier digestibility due to a lower degree of branching or a steric structure which restricts the accessibility for the enzymes employed could bring this about.

The other area in which starch is used as so-called native starch because of its polymeric structure is divided into two further fields of use:

1. Foodstuffs Industry

Starch is a classical additive for many foodstuffs, in which it essentially takes on the function of the binding of aqueous additives or causes an increase in the viscosity or else increased gel formation. Important characteristic features are the flow and sorption behavior, the swelling and gelatinization temperature, the viscosity and thickening power, the solubility of the starch, the transparency and gel structure, the heat, shear and acid stability, the proneness to retrogradation, the capacity for film formation, the freezing/thawing stability, the digestibility and the capacity for complex formation with, for example, inorganic or organic ions.

2. Non foodstuffs Industry

In this wide area, starch can be employed as an auxiliary for different production processes or as an additive in technical products. When using starch as an auxiliary, the paper and cardboard industry is to be mentioned here in particular. Starch primarily serves here for the retardation (retention of solids), the binding of filler and fine material particles, as a stiffener and for dehydration. Moreover, the favorable properties of the starch are utilized in relation to stiffness, hardness, sound, grip, gloss, smoothness, bonding strength and the surfaces.

2.1 Paper and Cardboard Industry

Within the paper manufacturing process, four application areas, namely surface, coating, mass and spraying, are to be differentiated. The demands on the starch in relation to the surface treatment are essentially a high degree of whiteness, a suitable viscosity, a high viscosity stability, good film formation and low dust formation. When used in coating, the solids content, a suitable viscosity, a high binding power and a high pigment affinity play an important role. As an additive to the mass, a rapid, uniform, loss-free distribution, high mechanical stability and complete retention in the paper web are of importance. When the starch is used in the spraying area, a suitable solids content, high viscosity and a high binding power are likewise of importance.

2.2 Adhesives Industry

A wide area of use of starches is in the adhesives industry, where the possibilities of use can be divided into four subareas: the use as pure starch size, the use in starch sizes prepared using special chemicals, the use of starch as an additive to synthetic resins and polymer dispersions, and the use of starches as extenders for synthetic adhesives. 90% of the adhesives based on starch are employed in the areas corrugated cardboard production, production of paper sacks, sachets and bags, production of composite materials for paper and aluminum, production of cardboard boxes and gum for envelopes, stamps etc.

2.3 Textile and Textile Care Compositions Industry

A wide area of use for starches as auxiliaries and additives is the production of textiles and textile care compositions area. Within the textile industry, the following four areas of use can be differentiated: the use of starch as a sizing agent, i.e. as an auxiliary for smoothing and strengthening the clinging behavior for protection against the tensile forces acting during weaving, and for increasing the abrasion resistance during weaving, starch as an agent for textile finishing, especially after quality-impairing pretreatments, such as bleaching, dyeing etc., starch as a thickener in the production of dye pastes for the prevention of dye diffusion, and starch as an additive to warping agents for sewing threads.

2.4 Building Materials Industry

The fourth area of use is the use of starches as additives in building materials. One example is the production of plasterboard sheets, in which the starch mixed in the plaster slurry gelatinizes with the water, diffuses to the surface of the plaster sheet and there binds the board to the sheet. Further areas of use are admixture to rendering and mineral fibers. In the case of ready-mixed concrete, starch products are used to delay setting.

2.5 Soil Stabilization

A further market for starch offers itself in the production of compositions for soil stabilization, which are employed for the temporary protection of the soil particles against water when the soil is moved artificially. According to present knowledge, combination products of starch and polymer emulsions are to be equated to the products previously employed in their erosion- and encrustation-decreasing action, but have markedly lower prices than these.

2.6 Use in Plant Protection Agents and Fertilizers

One area of use is the use of starch in plant protection agents for modifying the specific properties of the preparations. Thus starch can be employed for improving the wetting of plant protection agents and fertilizers, for the metered release of the active compounds, for the conversion of liquid, volatile and/or foul-smelling active compounds into microcrystalline, stable, shapeable substances, for mixing incompatible compounds and for extending the duration of action by decreasing decomposition.

2.7 Pharmaceuticals, Medicine and the Cosmetics Industry

A further area of use is the area of pharmaceuticals, medicine and the cosmetics industry. In the pharmaceutical industry, starch can be employed as a binder for tablets or for diluting the binder in capsules. Furthermore, starch can serve as a tablet disintegrant, as it absorbs liquid after swallowing and after a short time swells to such an extent that the active compound is released. Medicinal lubricating powders and wound powders are based on starch for reasons of quality. In the cosmetics area, starches are employed, for example, as carriers of powder additives, such as fragrances and salicylic acid. A relatively wide area of application for starch is in toothpaste.

2.8 Addition of Starch to Charcoal and Briquettes

One area of use of starch is as an additive to charcoal and briquettes. Charcoal can be agglomerated or made into briquettes of high grade quantitatively using the addition of starch, by means of which premature disintegration of the briquette is prevented. In the case of barbecue charcoal, the addition of starch is between 4 and 6%; in the case of calorized charcoal between 0.1 and 0.5%. In addition, starches are gaining importance as binders, as the emission of harmful substances can be markedly decreased by means of their addition to charcoal and briquettes.

2.9 Ore and Coal Slurry Preparation

Starch can furthermore be employed in ore and coal slurry preparation as a flocculant.

2.10 Foundry Auxiliary

A further area of use is as an additive to foundry auxiliaries. In various casting processes, cores are needed which are prepared from sands treated with binders. The binder used today is mainly bentonite, which is treated with modified starches, usually swellable starches.

The purpose of the addition of starch is increasing the flowability and improving the adhesiveness. Moreover, the swellable starches can be subject to further production engineering demands, such as being dispersible in cold water, rehydratable, readily miscible in sand and having high water binding capacity.

2.11 Use in the Rubber Industry

In the rubber industry, starch can be employed for improving the technical and optical quality. The reasons in this case are the improvement of the surface luster, the improvement of the grip and of the appearance (for this, starch is scattered onto the tacky gummed surfaces of rubber materials before cold vulcanization), and also the improvement of the printability of the rubber.

2.12 Production of Leather Substitutes

A further marketing possibility for the modified starches is the production of leather substitutes.

2.13 Starch in Synthetic Polymers

In the plastics sector, the following areas of use stand out: the inclusion of starch secondary products in the finishing process (starch is only a filler, there is no direct bond between the synthetic polymer and starch) or alternatively the inclusion of starch secondary products in the production of polymers (the starch and polymer form a permanent bond).

Compared with the other substances such as talc, the use of starch as a pure filler is not competitive. Things are different if the specific properties of starch come to bear and as a result the character profile of the final products is distinctly modified. An example of this is the use of starch products in the finishing of thermoplastics, such as polyethylene. The starch and the synthetic polymer here are combined by coexpression in the ratio of 1:1 to give a 'masterbatch', from which various products can be produced with granulated polyethylene using conventional process techniques. By the inclusion of starch in polyethylene films, an increased substance permeability in the case of hollow bodies, an improved water vapor permeability, an improved antistatic behavior, an improved antiblock behavior and an improved printability with aqueous dyes can be achieved.

Another possibility is the use of starch in polyurethane foams. With adaptation of the starch derivatives and by process engineering optimization, it is possible to control the reaction between synthetic polymers and the hydroxyl groups of these starches specifically. The result is polyurethane films which, owing to the use of starch, obtain the following characteristic profiles: a decrease in the heat expansion coefficients, decrease in the shrinkage behavior, improvement of the pressure/tension behavior, increase in the water vapor permeability without modification of water absorption, decrease in the flammability and tear density, no dropping of combustible parts, freedom from halogen and decreased aging. Disadvantages which are currently still present are decreased resistance to pressure and a decreased impact strength.

Product development, meanwhile, is no longer restricted only to films. Solid plastic products, such as pots, plates and dishes, can also be produced with a starch content of over 50%. In addition, starch/polymer mixtures are to be favorably assessed, as they have a very much higher biodegradability.

Starch graft polymers have furthermore gained extraordinary importance on account of their extreme water-binding ability. These are products having a backbone of starch and a side lattice of a synthetic monomer grafted on according to the principle of the free-radical chain mechanism. The starch graft polymers available today are distinguished by a better binding and retention capacity of up to 1000 g of water per g of starch combined with high viscosity. The application areas for these superabsorbers have greatly expanded in recent years and lie in the hygiene area with products such as diapers and pads, and in the agricultural sector with seed coatings, for example.

What is crucial for the use of the novel, genetically modified starches is, on the one hand, the structure, water content, protein content, lipid content, fiber content, ash/phosphate content, amylose/amylopectin ratio, molar mass distribution, degree of branching, particle size and shape and crystallinity, and on the other hand also the properties which lead to the following features: flow and sorption behavior, gelatinization temperature, viscosity, thickening power, solubility, gel structure and transparency, heat, shear and acid stability, proneness to retrogradation, gel formation, freeze/thaw stability, complex formation, iodine binding, film formation, adhesive power, enzyme stability, digestibility and reactivity.

The production of modified starches by means of genetic engineering interventions in a transgenic plant can on the one hand modify the properties of the starch obtained from the plant to the effect that further modifications by means of chemical or physical processes no longer appear necessary. On the other hand, the starches modified by genetic engineering processes can be subjected to further chemical and/or physical modifications, which leads to further improvements in the quality for certain of the areas of use described above. These chemical and physical modifications are known in principle. In particular, they are modifications by:

heat treatment,
acid treatment,
production of starch ethers
  starch alkyl ethers, O-allyl ethers, hydroxylalkyl ethers, O-carboxylmethyl ethers, N-containing starch ethers, P-containing starch ethers, S-containing starch ethers
production of crosslinked starches
production of starch graft polymers
oxidation and
esterifications which lead to the formation of phosphate, nitrate, sulfate, xanthate, acetate and citrate starches. Further organic acids can likewise be employed for esterification.

The figures show.

1. Starch Analysis Methods
a) Determination of the amylose/amylopectin ratio
  Starch was isolated from potato plants by standard methods, and the amylose to amylopectin ratio was determined according to the method described by Hovenkamp-Hermelink et al. (Potato Research 31, (1988), 241–246).
b) Determination of the Phosphate Content
  The positions C2, C3 and C6 of the glucose units can be phosphorylated in starch. For the determination of the phosphate group content at the C6 position, 100 mg of starch were hydrolyzed at 95° C. for 4 hours in 1 ml of 0.7 M HCl (Nielsen et al., Plant Physiol. 105, (1994), 11–117). After neutralization with 0.7 M KOH, 50 µl of the hydrolyzate were subjected to an optical enzymatic test for glucose 6-phosphate determination. The change in the absorption of the test batch (100 mM imidazole/HCl; 10 mM $MgCl_2$; 0.4 mM NAD; 2 units of glucose 6-phosphate dehydrogenase from *Leuconostoc mesenteroides*; 30° C.) was monitored at 334 nm.

The total phosphate content was determined according to the method of Ames (Methods in Enzymology VIII, (1966), 115–118).

About 50 mg of starch are treated with 30 µl of ethanolic magnesium nitrate solution and incinerated in a muffle furnace at 500° C. for three hours. The residue is treated with 300 µl of 0.5 M hydrochloric acid and incubated at 60° C. for 30 min.

An aliquot is then made up to 300 µl with 0.5 M hydrochloric acid, added to a mixture of 100 µl of 10% strength ascorbic acid and 600 µl of 0.42% ammonium molybdate in 2 M sulfuric acid and incubated at 45° C. for 20 min.

Photometric determination at 820 nm follows taking into account a phosphate calibration series as the standard.

c) Determination of the Gel Solidity (Texture Analyzer)
  2 g of starch (TS) are gelatinized in 25 ml of $H_2O$ (cf. RVA) and then stored at 25° C. in a sealed air-tight container for 24 h. The samples are fixed under the probe (round stamp) of a texture analyzer TA-XT2 from Stable Micro Systems and the gel solidity is determined using the following parameters:

| | |
|---|---|
| test speed | 0.5 mm/s |
| penetration depth | 7 mm |
| contact area | 113 $mm^2$ |
| pressure | 2 g | d) Viscosity Profile
  2 g of starch (TS) are taken up in 25 ml of $H_2O$ and used for analysis in a Rapid Visco Analyser (Newport Scientific Pty Ltd., Investmet Support Group, Warriewood NSW 2102, Australia). The apparatus is operated according to the instructions of the manufacturer. For determination of the viscosity of the aqueous solution of the starch, the starch suspension is first heated from 50° C. to 95° C. at a rate of 12° C. per minute. The temperature is then kept at 95° C. for 2.5 min. The solution is then cooled from 95° C. to 50° C. at a rate of 12° C. per minute. The viscosity is determined during the entire time.

The gelatinization temperature is determined by means of the gradient of the viscosity curve as a function of time. If the gradient of the curve is greater than 1.2 (this value is specified by the user), the computer program identifies the temperature measured at this point in time as the gelatinization temperature.

e) Determination of Glucose, Fructose and Sucrose

The content of glucose, fructose and sucrose is determined according to the method described by Stitt et al. (Methods in Enzymology 174, (1989), 518–552).

f) Analysis of the Side Chain Distribution of the Amylopectin

The side chain distribution, resp. length is determined as described in Lloyd et al., Biochem. J. 338, (1999), 515–521. The following elution conditions are chosen:

| Time min | 0.15 M NaOH % | 1 M NaAc in 0.15 M NaOH % |
|---|---|---|
| 0 | 100 | 0 |
| 5 | 100 | 0 |
| 20 | 85 | 15 |
| 35 | 70 | 30 |
| 45 | 68 | 32 |
| 60 | 0 | 100 |
| 70 | 0 | 100 |
| 72 | 100 | 0 |
| 80 | 100 | 0 | g) Particle Size Determination

The particle size determination was carried out using a photo-sedimentometer of the "Lumosed" type from Retsch GmbH, Germany.

The particle size distribution was determined in an aqueous solution and was carried out according to the manufacturer's instructions and based on the literature of, for example, H. Pitsch, particle size determination; LABO-1988/3 Technical Journal for Laboratory Technology, Darmstadt.

h) Water-binding Ability

For the determination of the water-binding ability, the residue was weighed after the separation of the soluble portion by centrifugation of the starch swollen at 70° C. The water-binding ability (WBA) of the starch was related to the initial starch weight corrected by the soluble mass.

$WBA(g/g)$=(residue−(initial weight−soluble portion))/(initial weight−soluble portion)

The following vectors were used in the examples:

Details of the Vector pBinAR-Hyg

The plasmid pBinAR is a derivative of the binary vector plasmid pBin19 (Bevan, 1984), which was constructed in the following manner:

a fragment 529 bp long which comprises the nucleotides 6909–7437 of the 35S promoter of the cauliflower mosaic virus was isolated as the EcoR I/Kpn I fragment from the plasmid pDH51 (Pietrzak et al., 1986) and ligated between the EcoR I and Kpn I cleavage sites of the polylinker of pUC18. The plasmid pUC18-35S was formed. From the plasmid pAGV40 (Herrera-Estrella et al., 1983), with the aid of the restriction endonucleases Hind III and Pvu II a fragment 192 bp long was isolated which comprises the polyadenylation signal (3' end) of the octopin synthase gene (gene 3) of the T DNA of the Ti plasmid pTiACH5 (Gielen et al., 1984) (nucleotides 11749–11939). After addition of Sph I linkers to the Pvu II cleavage site, the fragment was ligated between the Sph I and Hind III cleavage sites of pUC18-35S. The plasmid pA7 resulted from this. Starting from the plasmid pA7, the EcoRI Hind III fragment containing the 35S RNA promoter, the ocs terminator and the part of the polylinker situated between the 35S RNA promoter and the ocs element was ligated into the appropriately cleaved pBIB-Hyg plasmid (Becker, 1990).

The following examples illustrate the invention without restricting it in any way.

EXAMPLE 1

Production of Transgenic Potato Plants which Have a Decreased Activity of a GBSSI and of a BEI protein For the production of transgenic plants which have a decreased activity of a GBSSI and of a BEI protein, transgenic plants were first produced which had a decreased GBSSI activity. For this purpose, the T-DNA of the plasmid pB33aGBSSI-Kan was transferred to potato plants with the aid of agrobacteria, as described in Roch-Sosa et al. (EMBO J. 8, (1989), 23–29).

For the construction of the plasmid pB33aGBSSI-Kan, the DraI/DraI fragment from the promoter region of the patatin class I gene B33 of Solanum tuberosum, comprising the nucleotides —1512 to +14 (Rocha-Sosa et al., (1989), see above) was ligated into the SmaI cleavage site of the plasmid pUC19 (Genbank Acc. No. M77789). From the resulting plasmid, the promoter fragment was ligated as EcoRI/HindIII fragment into the polylinker region of the plasmid pBin19 (Bevan et al., Nucl Acids Res 11, (1983), 369–385). The 3'EcoRI fragment, nucleotides +1181 to +2511 of the GBSSI gene from Solanum tuberosum (Hergersberg, Molecular analysis of the waxy gene from Solanum tuberosum and expression of waxy antisense RNA in potatoes. Dissertation at University of Cologne (1988)) was then ligated into the EcoRI cleavage site of the resulting plasmid. The plasmid pB33aGBSSI-Kan resulted.

After the transformation, various lines of transgenic potato plants were identified which had a markedly decreased content of the mRNA of a GBSSI and a decreased activity of the GBSSI protein. Plants of this type furthermore synthesize a starch having an amylopectin content of at least 90%.

Two independent lines of these amylopectin-synthesizing plants were then transformed using the plasmid p35SaBEI-Hyg. For the construction of this plasmid, a SmaI/HindIII fragment about 3000 bp long, containing a partial cDNA for the BEI enzyme from potato (Kossmann, cloning and functional analysis of genes coding for proteins involved in the carbohydrate exchange of the potato, Dissertation Technical University Berlin, (1992)) was smoothed out and inserted in antisense orientation with respect to the 35S promoter into the SmaI cleavage site of the vector pBinAR-Hyg (see above).

After the supertransformation, various independent lines were identified which indeed contained the same T-DNAs, but integrated at different sites in the genome, which had both a decreased GBSSI activity and a significantly decreased amount of BEI-mRNA. Plants were selected which, in comparison to corresponding wild-type plants, have an enzyme activity of the GBSSI protein reduced by preferably at least 95% and an enzyme activity of the BEI protein reduced by at least 90%. The starches of these plants were then analyzed.

EXAMPLE 2

Analysis of the Starch from Plants Having Decreased GBSSI and BEI Activity

The starch formed by the transgenic potato plants produced according to Example 1 differs, for example, from starch synthesized in wild-type plants in its phosphate or amylose content and in the viscosity and gelatinization properties determined by means of RVA. The results of the physico-chemical characterization of the modified starches are shown in Table 1 (Tab. 1).

TABLE 1

| No. | Geno-type | Phosphate in C6 (%) | Total phosphate (%) | Amylose (%) | RVA Max (%) | RVA Min (%) | RVA Fin (%) | RVA Set (%) | RVA T (%) | Gel solidity (%) |
|---|---|---|---|---|---|---|---|---|---|---|
| 1 | Desiree (wild-type) | 100 | 100 | 22 | 100 | 100 | 100 | 100 | 100 | 100 |
| 2 | AsGBSSI | 110 | 119 | <4 | 70 | 90 | 84 | 57 | 104 | 21 |
| 3 | AsBEI | | 170 | 20 | 124 | 94 | 90 | 76 | 100 | 91 |
| 4 | AsGBSSI-asBEI | 181 | 189 | <4 | 69 | 84 | 78 | 51 | 102 | 21 |

Legend:
GBSSI = granule-bound starch synthase I
BEI = branching enzyme I
as = antisense
RVA = Rapid Visco Analyser
Max = maximum viscosity
Min = minimum viscosity
Fin = viscosity at the end of the measurement
Set = setback = difference between Min and Fin
T = gelatinization temperature With the exception of the amylose content, the % values are based on the wild type (=100%).

What is claimed is:

1. A transgenic potato plant cell which is genetically modified, the genetic modification leading to a decrease in the activity of one or more granule-bound starch synthase I (GBSSI) proteins occurring endogenously in the plant cell and to a decrease in the activity of one or more branching enzyme I (BEI) proteins occurring endogenously in the plant cell, in comparison to corresponding non genetically modified plant cells of wild type plants, wherein said genetic modification comprises the introduction of a foreign nucleic acid molecule which comprises DNA molecules selected from the group consisting of:

(a) DNA molecules which encode at least one antisense RNA which brings about a decrease in the expression of endogenous genes encoding GBSSI and BEI proteins;

(b) DNA molecules which lead, via a cosuppression effect, to a decrease in the expression of endogenous genes encoding GBSSI and BEI proteins;

(c) DNA molecules which encode at least one antisense RNA which brings about a decrease in the expression of endogenous genes encoding GBSSI and which encode at least one sense RNA which leads, via a cosuppression effect, to a decrease in the expression of endogenous genes encoding BEI proteins; and (d) DNA molecules which encode at least one antisense RNA which brings about a decrease in the expression of endogenous genes encoding BEI and which encode at least one sense RNA which leads, via a cosuppression effect, to a decrease in the expression of endogenous genes encoding GBSSI proteins;

wherein said DNA molecules contain a sequence with a homology of between 95% and 100% to an endogenous gene encoding BEI protein and a sequence with a homology of between about 95% and 100% to an endogenous gene encoding GBSSI protein.

2. A transgenic potato plant cell which is genetically modified, the genetic modification leading to a decrease in the activity of one or more granule-bound starch synthase I (GBSSI) proteins occurring endogenously in the plant cell and to a decrease in the activity of one or more branching enzyme I (BEI) proteins occurring endogenously in the plant cell, in comparison to corresponding non genetically modified plant cells of wild type plants, wherein said genetic modification comprises the introduction of two foreign nucleic acid molecules, in which said two foreign nucleic acid molecules are selected from the group consisting of:

(a) one DNA molecule containing a sequence with a homology of between 95% and 100% to an endogenous gene encoding GBSSI protein which encodes at least one antisense RNA which brings about a decrease in the expression of endogenous genes encoding GBSSI and one DNA molecule containing a sequence with a homology of between 95% and 100% to an endogenous gene encoding BEI protein which encodes at least one antisense RNA which brings about a decrease in the expression of endogenous genes encoding BEI proteins;

(b) one DNA molecule containing a sequence with a homology of between 95% and 100% to an endogenous gene encoding GBSSI protein which leads, via a cosuppression effect, to a decrease in the expression of endogenous genes encoding GBSSI and one DNA molecule containing a sequence with a homology of between 95% and 100% to an endogenous gene encoding BEI protein which leads, via cosuppression effect, to a decrease in the expression of endogenous genes encoding BEI proteins;

(c) one DNA molecule containing a sequence with a homology of between 95% and 100% to an endogenous gene encoding GBSSI protein which encodes at least one antisense RNA which brings about a decrease in the expression of endogenous genes encoding GBSSI and one DNA molecule containing a sequence with a homology of between 95% and 100% to an endogenous gene encoding BEI protein which encodes at least one sense RNA and which leads, via a cosuppression effect, to a decrease in the expression of endogenous genes encoding BEI proteins; and (d) one DNA molecule containing a sequence with a homology of between 95% and 100% to an endogenous gene encoding BEI protein which encodes at least one antisense RNA which brings about a decrease in the expression of endogenous genes encoding BEI and one DNA molecule containing a sequence with a homology of between 95% and 100% to an endogenous gene encoding GBSSI protein which encodes at least one sense RNA and which leads, via a cosuppression effect, to a decrease in the expression of endogenous genes encoding GBSSI proteins.

3. The transgenic potato plant cell as claimed in claim 1 or 2, which synthesizes a modified starch having an amylopectin content of at least 90% and having an increased phosphate content in comparison to starch from plant cells of corresponding potato plants of the waxy phenotype.

4. A process for the production of a transgenic potato plant cell which synthesizes a modified starch, in which a potato plant cell is genetically modified by the introduction of one foreign nucleic acid molecule, wherein the presence and/or expression of the foreign nucleic acid molecule leads to a decrease in the activity of at least one GBSSI protein and to a decrease in the activity of at least one BEI protein, in which said foreign nucleic acid molecule comprises DNA molecules selected from the group consisting of:

(a) DNA molecules which encode at least one antisense RNA which brings about a decrease in the expression of endogenous genes encoding GBSSI and BEI proteins;

(b) DNA molecules which lead, via a cosuppression effect, to a decrease in the expression of endogenous genes encoding GBSSI and BEI proteins;

(c) DNA molecules which encode at least one antisense RNA which brings about a decrease in the expression of endogenous genes encoding GBSSI and which encode at least one sense RNA which leads, via a cosuppression effect, to a decrease in the expression of endogenous genes encoding BEI proteins; and (d) DNA molecules which encode at least one antisense RNA which brings about a decrease in the expression of endogenous genes encoding BEI and which encode at least one sense RNA which leads, via a cosuppression effect, to a decrease in the expression of endogenous genes encoding GBSSI proteins;

wherein said DNA molecules contain a sequence with a homology of between 95% and 100% to an endogenous gene encoding BEI protein and a sequence with a homology of between 95% and 100% to an endogenous gene encoding GBSSI protein.

5. A process according to claim 4, wherein the modified potato starch has an amylopectin content of at least 90% and an increased phosphate content in comparison to starch from corresponding potato plants of the waxy phenotype.

6. A process for the production of a transgenic potato plant which synthesizes a modified starch, wherein:

(a) a potato plant cell is genetically modified by the introduction of one foreign nucleic acid molecule wherein the presence and/or expression of the foreign nucleic acid molecule leads to a decrease in the activity of at least one GBSSI protein and to a decrease in the activity of at least one BEI protein; in which said nucleic acid molecule comprises DNA molecules selected from the group consisting of:

(i) DNA molecules which encode at least one antisense RNA which brings about a decrease in the expression of endogenous genes encoding GBSSI and BEI proteins;

(ii) DNA molecules which lead, via a cosuppression effect, to a decrease in the expression of endogenous genes encoding GBSSI and BEI proteins;

(iii) DNA molecules which encode at least one antisense RNA which brings about a decrease in the expression of endogenous genes encoding GBSSI and which encode at least one sense RNA which leads via a cosuppression effect, to a decrease in the expression of endogenous genes encoding BEI proteins; and (iv) DNA molecules which encode at least one antisense RNA which brings about a decrease in the expression of endogenous genes encoding BEI and which encode at least one sense RNA which leads via a cosuppression effect, to a decrease in the expression of endogenous genes encoding GBSSI proteins;

wherein said DNA molecules contain a sequence with a homology of between 95% and 100% to an endogenous gene encoding BEI protein and a sequence with a homology of between 95% and 100% to an endogenous gene encoding GBSSI protein;

(b) a potato plant is regenerated from the cell according to step a); and (c) optionally, further potato plants are produced from the plants produced according to step b).

7. The process according to claim 6, wherein the modified potato starch has an amylopectin content of at least 90% and an increased phosphate content in comparison to starch from corresponding potato plants of the waxy phenotype.

8. A transgenic potato plant comprising potato plant cells as claimed in claim 1 or 2.

9. A reproductive material of a potato plant, wherein said reproductive material comprises potato plant cells as claimed in claim 1 or 2.

10. A composition comprising at least one of the nucleic acid molecules as defined in claim 1 or 2, which is suitable for the production of transgenic potato plant cells as claimed in claim 1 or 2, the presence of said nucleic acid molecules in said potato plant cells leading to a decrease in the activity of GBSSI proteins occurring endogenously in the potato plant cell and to a decrease in the activity of BEI proteins occurring endogenously in the potato plant cell.

11. The composition as claimed in claim 10, the nucleic acid molecule(s) being contained in a recombinant nucleic acid molecule.

12. A host cell containing a composition as claimed in claim 10.

13. A transgenic potato plant cell containing a composition as claimed in claim 10.

14. A process for the production of a modified potato starch from a transgenic potato plant, comprising extracting the starch from the potato plant according to claim 8.

15. The process of claim 14, wherein the modified potato starch has an amylopectin content of at least 90% and an increased phosphate content in comparison with starch from corresponding potato plants of the waxy phenotype.

16. The process of claim 15, wherein the modified potato starch has a decreased gelatinization temperature in comparison with starch from corresponding potato plants of the waxy phenotype.

17. A process for the production of a transgenic potato plant cell which synthesizes a modified starch, in which a potato plant cell is genetically modified by the introduction of two foreign nucleic acid molecules, wherein the presence and/or expression of the foreign nucleic acid molecules lead to a decrease in the activity of at least one GBSSI protein and to a decrease in the activity of at least one BEI protein, in which said foreign nucleic acid molecules are selected from the group consisting of:
   (a) one DNA molecule containing a sequence with a homology of between 95% and 100% to an endogenous gene encoding GBSSI protein which encodes at least one antisense RNA which brings about a decrease in the expression of endogenous genes encoding GBSSI and one DNA molecule containing a sequence with a homology of between 95% and 100% to an endogenous gene encoding BEI protein which encodes at least one antisense RNA which brings about a decrease in the expression of endogenous genes encoding BEI proteins;
   (b) one DNA molecule containing a sequence with a homology of between 95% and 100% to an endogenous gene encoding GBSSI protein, which leads, via a cosuppression effect, to a decrease in the expression of endogenous genes encoding GBSSI and one DNA molecule containing a sequence with a homology of between 95% and 100% to an endogenous gene encoding BEI protein which leads, via a cosuppression effect, to a decrease in the expression of endogenous genes encoding BEI proteins;
   (c) one DNA molecule containing a sequence with a homology of between 95% and 100% to an endogenous gene encoding GBSSI protein which encodes at least one antisense RNA which brings about a decrease in the expression of endogenous genes encoding GBSSI and one DNA molecule containing a sequence with a homology of between about 95% and 100% to an endogenous gene encoding BEI protein which encodes at least one sense RNA and which leads, via a cosuppression effect, to a decrease in the expression of endogenous genes encoding BEI proteins; and
   (d) one DNA molecule containing a sequence with a homology of between 95% and 100% to an endogenous gene encoding BEI protein which encodes at least one antisense RNA which brings about a decrease in the expression of endogenous genes encoding BEI and one DNA molecule containing a sequence with a homology of between about 95% and 100% to an endogenous gene encoding GBSSI protein which encodes at least one sense RNA and which leads, via a cosuppression effect, to a decrease in the expression of endogenous genes encoding GBSSI proteins.

18. The process according to claim 17, wherein the modified potato starch has an amylopectin content of at least 90% and an increased phosphate content in comparison to starch from corresponding potato plants of the waxy phenotype.

19. A process for the production of a transgenic potato plant which synthesizes a modified starch, in which:

(a) a potato plant cell is genetically modified by the introduction of two foreign nucleic acid molecules wherein the presence and/or expression of the foreign nucleic acid molecules lead to a decrease in the activity of at least one GBSSI protein and to a decrease in the activity of at least one BEI protein; in which said nucleic acid molecules are selected from the group consisting of:
      (i) one DNA molecule containing a sequence with a homology of between 95% and 100% to an endogenous gene encoding GBSSI protein which encodes at least one antisense RNA which brings about a decrease in the expression of endogenous genes encoding GBSSI and one DNA molecule containing a sequence with a homology of between 95% and 100% to an endogenous gene encoding BEI protein which encodes at least one antisense RNA which brings about a decrease in the expression of endogenous genes encoding BEI proteins;
      (ii) one DNA molecule containing a sequence with a homology of between 95% and 100% to an endogenous gene encoding GBSSI protein, which leads, via a cosuppression effect, to a decrease in the expression of endogenous genes encoding GBSSI and one DNA molecule containing a sequence with a homology of between 95% and 100% to an endogenous gene encoding BEI protein which leads, via a cosuppression effect, to a decrease in the expression of endogenous genes encoding BEI proteins;
      (iii) one DNA molecule containing a sequence with a homology of between 95% and 100% to an endogenous gene encoding GBSSI protein which encodes at least one antisense RNA which brings about a decrease in the expression of endogenous genes encoding GBSSI and one DNA molecule containing a sequence with a homology of between 95% and 100% to an endogenous gene encoding BEI protein which encodes at least one sense RNA and which leads, via a cosuppression effect, to a decrease in the expression of endogenous genes encoding BEI proteins; and
      (iv) one DNA molecule containing a sequence with a homology of between 95% and 100% to an endogenous gene encoding BEI protein which encodes at least one antisense RNA which brings about a decrease in the expression of endogenous genes encoding BEI and one DNA molecule containing a sequence with a homology of between 95% and 100% to an endogenous gene encoding GBSSI protein which encodes at least one sense RNA and which leads, via a cosuppression effect, to a decrease in the expression of endogenous genes encoding GBSSI proteins;
   (b) a potato plant is regenerated from the cell produced according to step a); and,
   (c) optionally, further potato plants are produced from the plants produced according to step b).

20. A process according to claim 19, wherein the modified potato starch has an amylopectin content of at least 90% and an increased phosphate content in comparison to starch from corresponding potato plants of the waxy phenotype.

* * * * *